United States Patent [19]

Ronkainen et al.

[11] 4,415,659
[45] Nov. 15, 1983

[54] METHOD FOR MASHING STARCH-RICH MATERIAL FOR ALCOHOL PRODUCTION

[75] Inventors: Pentti P. Ronkainen, Espoo; Olavi A. Leppänen; Kai J. Harju, both of Helsinki; Pertti J. Eräpolku, Rajamäki, all of Finland

[73] Assignee: Oy Alko AB, Helsinki, Finland

[21] Appl. No.: 341,933

[22] Filed: Jan. 22, 1982

[30] Foreign Application Priority Data

Feb. 5, 1981 [FI] Finland ................................. 810344

[51] Int. Cl.³ .......................... C12P 1/00; C12P 7/06; C12C 7/04
[52] U.S. Cl. ...................................... 435/161; 426/29; 426/447; 426/508; 435/93
[58] Field of Search .......................... 435/161, 162, 93; 426/29, 508, 518, 447, 449

[56] References Cited

U.S. PATENT DOCUMENTS 2,348,451 5/1944 Christensen ........................ 435/161
3,576,645 4/1971 Rozsa .................................... 426/29
3,580,728 5/1971 Gulstad et al. ................. 426/449 X
4,350,714 9/1982 Duvall ........................... 426/449 X

OTHER PUBLICATIONS

De Clerck, J. A. Textbook of Brewing, vol. 1, Chapman & Hall Ltd., London, 1957 (pp. 319).
Altsheler, et al., Design of A Two-Bushel per Day Continuous Alcohol Unit, Chem. Eng. Progress, vol. 42, No. 9, 1947 (pp. 467-472).

*Primary Examiner*—David M. Nafe
*Attorney, Agent, or Firm*—Jordan and Hamburg

[57] ABSTRACT

This invention relates to a method for mashing starch-rich material, for example whole grain or partially crushed grain, when manufacturing alcohol. The method has a very low energy consumption, because the amount of water added to the starch-rich material in the beginning of the mashing stage is low. High pressure steam and a short processing time are used to keep the starch-rich material to water ratio during the processing stage below 1:2 because very little water is condensed from the water vapor during a short period. The mashed material is finally broken down by "shooting" the material from the reactor by using pressurized air.

2 Claims, 1 Drawing Figure

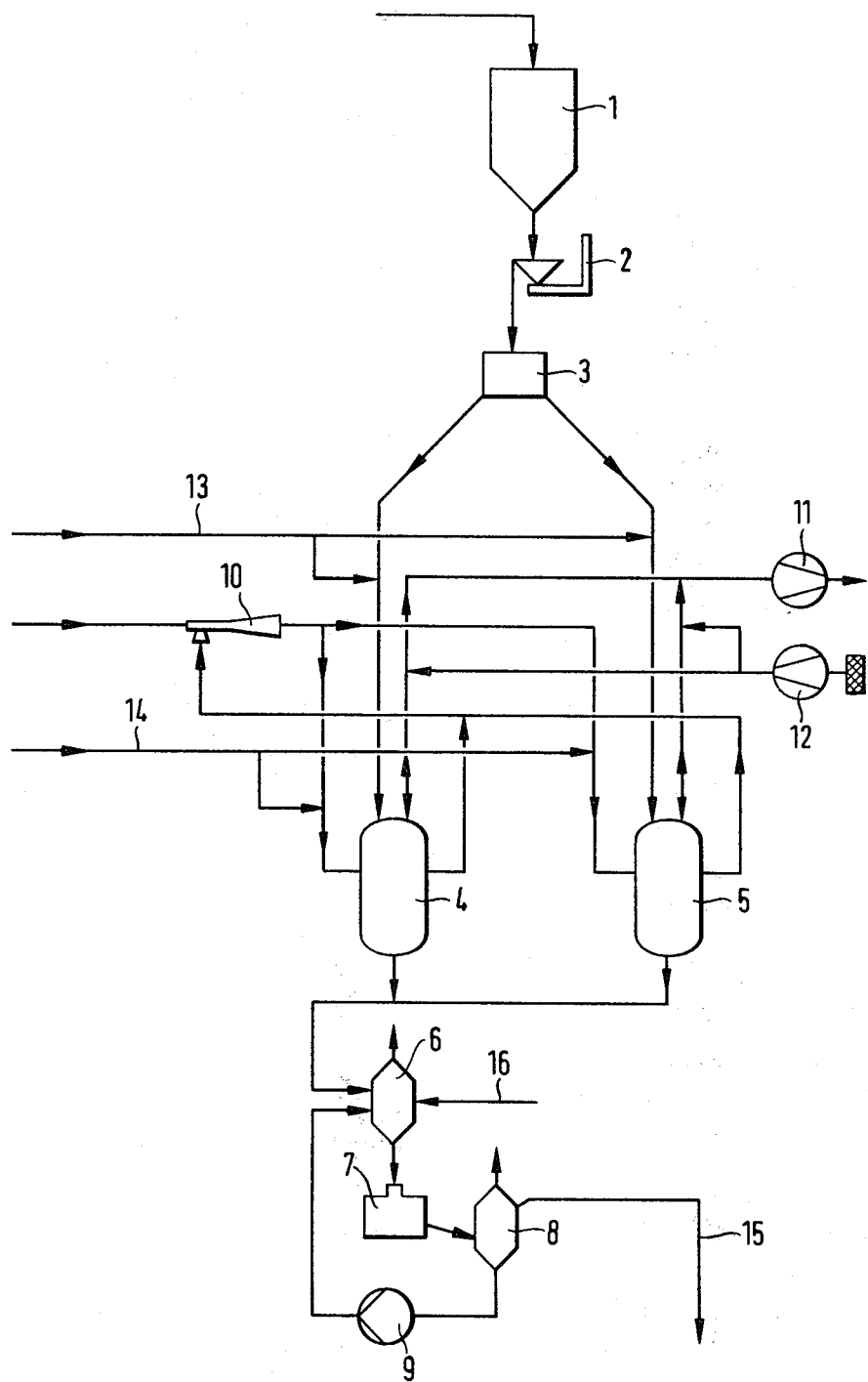

METHOD FOR MASHING STARCH-RICH MATERIAL FOR ALCOHOL PRODUCTION

BACKGROUND OF THE INVENTION

1. Field of the Invention

This invention is concerned with a mashing method with the aid of which remarkable savings can be attained in relation to the energy consumption required by the process. According to the invention, the basic method is the alternating use of reactors so that the released reactor steam is led into a parallel reactor to be used as a part of steaming of the grain charge. The same procedure is also performed with the steam from the other reactor, in other words it is led into the first reactor in its turn. 2. Description of the Prior Art The use of grain as a raw material in alcohol production usually comprises the following procedures:
grain processing and grinding or crushing
mash cooking of the floour or crushings
fluidisation and sugaring of the starch
sugar fermentation into alcohol
alcohol distillation from the fermented wort
handling and drying the distilling wastes for fodder.

Of the above mentioned process stages the amount of energy consumed in mash cooking is considerable and for this reason efforts have been made by various means to reduce this.

Thus far the method which has been recognised as the most economical is the so called spray condensation method in which the expanded steam is led into a container or several containers into which the raw mash going to cooking is sprayed. Part of the steam condenses into the mash whereupon the mash temperature and its moisture content are increased. With this method of mashing the energy consumption in continuous cooking is about 0.71 MJ per kilo of grain.

It has been demonstrated that by using a heat exchanger to utilize the heat of the boiled mash to heat that mash which is being fed in, the energy consumption in ideal conditions would only be about 0.14 MJ per kilo of grain. The only extra energy requirement would then be needed for compensation of heat losses. For natural reasons it has not been possible to create this kind of circumstances. The pressure losses and fouling of heat exchangers lead to the actual energy consumption being noticeably larger.

The large amount of heat used in mashing methods is related to the large water content in the mash which makes the efficient utilisation of heat difficult. The grain to water ratio is commonly between 1:3.5 and 1:4. It is natural, then, that a reduction in water content in the mash would be advantageous when lowering energy consumption. A limitation to the reduction of the water content is however set, in that if too little water is used neither flour or crushings yield more than a tough putty-like substance the further processing of which is exceedingly difficult if not impossible.

SUMMARY OF THE INVENTION

The basic concept of the invention is that it has been observed that whole grain or a partially crushed grain is extremely well suited as a raw material for continuous charge cooking. Whole grain wheat binds, when saturated with water, about 0.7–1.7 parts of water to one part of wheat by weight. As the water content needed for the hydrolysis of the starch content in the grain is in principle insignificant, it is plain that the hydration occurring beneath the shell of the whole grain corn makes it possible to use only a really small amount of water at the softening stage and the large quantity of water needed at the fermentation stage is added after the softening stage.

As the grain is inside the shell during the whole of the softening stage no harmful material puttying (cementation) can occur in the method according to the invention. Partially crushed grain acts very well too and no significant puttying exists during softening. The softened grain is broken according to the invention by forcibly exhausting it out of the reactor by using pressurized air for example.

BRIEF DESCRIPTION OF THE DRAWINGS

The invention is illustrated in the following passage by describing the process stages and referring to the accompanying schematic drawing, which illustrates a preferred embodiment of the present invention.

DESCRIPTION OF THE PREFERRED EMBODIMENTS

The raw material travels from silo 1 through the load scales 2 and distributor 3 to reactors 4 and 5. After reactor 4 has been filled with raw material, pressure is reduced down to 0.01 MPa using vacuum pump 11, after which a small quantity of water at 70°–90° C. is added to the reactor along pipe 13 followed by steam at 0.7 MPa through pipe 14. Steaming at 0.7 MPa pressure lasts 5 minutes, during which time raw material is fed into reactor 5, vacuum introduced and a small quantity of water added at 70°–90° C. The steam from reactor 4 is then allowed to break into reactor 5 whereupon both are stabilised at an identical pressure of 0.1–0.2 MPa. Reactor 5 is pre-steamed with high-pressure steam (1.4 MPa) through ejector 10. Steam is drawn out of reactor 4 with the ejector, until the temperature there has fallen to 90°–100° C. After this the high-pressure steam is shut off and reactor 5 steamed for 5 minutes with steam at 0.7 MPa. Pressurized air is then led into reactor 4 from compressor 12, until pressure has risen to 1.5 MPa and the contents explosively ejected into a cyclone 6. The soft grains, broken down in their explosive ejection from the reactor, are rinsed out of the cyclone with an enzyme-containing dilution water fed through pipe 16, into the homogeniser 7 and then on to the equalising tank 8, from the bottom of which pump 9 conveys mash back to cyclone 6 and part of the mash goes from equalisation tank 8 as overflow along passage 15. The process cycle begins again after the reactor 4 has been emptied.

EXAMPLE

Experiments have been carried out with laboratory equipment which was constructed according to the previously presented basic layout and in which the volume of each reactor was 5 liters. As test material whole grain wheat was used, in which the moisture content was 11.7% and the starch content 55.4 %. In each charge at the beginning of the experiment, the grain to water ratio was 1 kg wheat to 0.5 kg water (gross weight 1.5 kg) and after the process cycle exhaust stage the total weight of the mixture was 1.7 kg. From the mash thus obtained a fermentable mash was made using added water and a screw homogeniser. In this fermentable mash dry material content was 19% (experiment 1) and 18.6% (experiment 2) and from which after sugaring, fermentation and distillation the alcohol amount obtained was 32.3 g (experiment 1) and 32.2 (experiment 2) per 100 g of dry wheat material. The alcohol yields obtained were equivalent to yields normally obtained in laboratory experiments and in industrial production.

The energy consumed in the experiments was below 0.4 MJ per kilo of grain. In addition the energy consumption associated with grain flouring and crushing was avoided and so was avoided also the enzyme additions before cooking which are really essential to the normal process. According to the invention, additional to the advantages of the process is the avoidance of pipe washing with acid and alkaline or time-consuming pipe drill-cleaning. These stages being otherwise necessary inconveniences in the reactor pipework and causing considerable waste water amounts to flow to the nature.

What is claimed is:

1. Method for mashing raw starch-rich material used in alcohol manufacture which comprises introducing whole or partially crushed raw starch-rich material into a reactor, reducing the pressure in the reactor to about 0.01 MPa, introducing heated water into the reactor followed by steam at about 0.7 MPa pressure and steaming the material in the reactor at about 0.7 MPa pressure for about 5 minutes, the water to starch-rich material ratio being maintained during the whole mashing time below 2:1, withdrawing steam from the reactor until the temperature in said reactor has fallen to 90°–100° C., introducing pressurized air into said reactor until the pressure therein has risen to about 1.5 MPa, and explosively ejecting the starch material from said reactor whereby soft grains therein are broken down.

2. Method according to claim 1, wherein the steaming is done alternately, using several reactors, the steam exhausted out of one reactor being led into another reactor and vice versa.

* * * * *